(12) United States Patent
Ise et al.

(10) Patent No.: US 9,157,905 B2
(45) Date of Patent: Oct. 13, 2015

(54) METHOD FOR IDENTIFYING ONCOGENE, METHOD FOR ESTABLISHING ONCOGENE-EXPRESSING CELL, AND METHOD OF SCREENING ONCOGENE TARGETING DRUG

(75) Inventors: Nobuyuki Ise, Tokyo (JP); Kazuya Omi, Tokyo (JP); Daisuke Nambara, Tokyo (JP)

(73) Assignee: FUJIREBIO INC., Tokyo (JP)

( * ) Notice: Subject to any disclaimer, the term of this patent is extended or adjusted under 35 U.S.C. 154(b) by 185 days.

(21) Appl. No.: 13/580,207

(22) PCT Filed: Feb. 21, 2011

(86) PCT No.: PCT/JP2011/053647
§ 371 (c)(1),
(2), (4) Date: Aug. 21, 2012

(87) PCT Pub. No.: WO2011/102507
PCT Pub. Date: Aug. 25, 2011

(65) Prior Publication Data
US 2012/0315628 A1 Dec. 13, 2012

(30) Foreign Application Priority Data
Feb. 22, 2010 (JP) ................................. 2010-036483

(51) Int. Cl.
| | | |
|---|---|---|
| C12N 15/00 | (2006.01) | |
| C12N 15/86 | (2006.01) | |
| C12N 15/87 | (2006.01) | |
| C12N 5/00 | (2006.01) | |
| C12N 5/071 | (2010.01) | |
| G01N 33/50 | (2006.01) | |
| C12N 5/09 | (2010.01) | |
| C12Q 1/48 | (2006.01) | |

(52) U.S. Cl.
CPC .......... *G01N 33/5011* (2013.01); *C12N 5/0693* (2013.01); *C12Q 1/48* (2013.01); *G01N 33/5023* (2013.01); *C12N 2501/998* (2013.01)

(58) Field of Classification Search
None
See application file for complete search history.

(56) References Cited

U.S. PATENT DOCUMENTS

| | | | | |
|---|---|---|---|---|
| 8,592,206 | B2 * | 11/2013 | Rustgi et al. ................... | 435/325 |
| 2008/0090776 | A1 | 4/2008 | Mano et al. | |
| 2008/0312096 | A1 * | 12/2008 | Gray et al. ........................ | 506/9 |

FOREIGN PATENT DOCUMENTS

| | | |
|---|---|---|
| JP | 2010 501175 | 1/2010 |
| WO | 03 012087 | 2/2003 |

OTHER PUBLICATIONS

Partin et al 1988. Cancer Res. 48:6050-6053.*
Lodish et al. 2000. Mol Cell Biol. 4th ed (WH Freeman, publisher) section 24.3.*
Masuda, M., et al., "Stet3 o Tokeibugan Chiryo no Bunshi Hyoteki to suru Rironteki Konkyo-Stat3 wa Tokeibugan no Achilles-ken ka?", Jibi to Rinsho, vol. 54, pp. 227 to 234, (Sep. 20, 2008), (with partial English translation).
Toyooka, S., et al., "Molecular Biology of Lung Cancer," Japanese Journal of Lung Cancer, vol. 50, No. 4, pp. 329 to 341 and 420, (Aug. 20, 2010) (with English abstract).
Soda, M., et al., "Identification of the transforming EML4-ALK fusion gene in non-small-cell lung cancer," Nature, vol. 448, pp. 561 to 567, (Aug. 2, 2007).
International Search Report Issued May 17, 2011 in PCT/JP11/053647 Filed Feb. 21, 2011.
Extended Search Report issued Aug. 9, 2013 in European Patent Application No. 11744793.8.
Michal Firon, et al., "Dominant negative Met reduces tumorigenicity-metastasis and increases tubule formation in mammary cells", Oncogene, nature Publishing group, vol. 19, No. 20, May 11, 2000, XP002371736, pp. 2386-2397.
Roberta Maestro, et al, "twist is a potential oncogene that inhibits apoptosis", Genes & Development, vol. 13, No. 17, Sep. 1, 1999, XP002700157, pp. 2207-2217.
Natasha Kyprianou, et al., "Relationship between Metastatic Ability and H-ras Oncogene Expression in Rat Mammary Cancer Cells Transfected with the v-H-ras Oncogene", Cancer Research, vol. 50, No. 5, 1990, XP002700158 pp. 1449-1454.
Office Action issued May 12, 2014 in European Patent Application No. 11 744 793.8.
Itai Pashtan, et al., "Targeting Hsp90 prevents escape of breast cancer cells from tyrosine kinase inhibition", Cell Cycle, vol. 7, No. 18, XP-002637559, Sep. 15, 2008, pp. 2936-2941.

* cited by examiner

*Primary Examiner* — Shulamith H Shafer
(74) *Attorney, Agent, or Firm* — Oblon, McClelland, Maier & Neustadt, L.L.P.

(57) ABSTRACT

The present invention provides a methodology that can develop a more excellent anti-cancer drug than conventional ones for various cancers. Specifically, the present invention provides a method for establishing an artificial cell, comprising treating a cancer cell with an expression vector for a foreign oncogene and then culturing the cancer cell treated with the expression vector under a condition which inhibits an expression or function of an oncogene that is inherent to the cancer cell, and an established artificial cell; a method of screening an anti-cancer drug, comprising evaluating whether or not a test substance inhibits a proliferation of the artificial cell; as well as a method for identifying an oncogene, comprising treating a cancer cell with an expression vector for a test gene and then culturing the cancer cell treated with the expression vector under a condition which inhibits an expression or function of an oncogene that is inherent to the cancer cell.

10 Claims, 7 Drawing Sheets

METHOD FOR IDENTIFYING ONCOGENE, METHOD FOR ESTABLISHING ONCOGENE-EXPRESSING CELL, AND METHOD OF SCREENING ONCOGENE TARGETING DRUG

TECHNICAL FIELD

The present invention relates to a method for identifying an oncogene, a method for establishing an oncogene-expressing cell, and a method of screening an oncogene targeting drug.

BACKGROUND ART

Currently, anti-cancer drugs are actively researched and developed. Effective techniques for research and development of the anti-cancer drugs may include (1) identification of an oncogene, (2) establishment of an oncogene-expressing cell, and (3) screening for an oncogene targeting drug.

(1) Identification of Oncogene

Anti-tumor effects of molecular targeting drugs that targets a particular oncogene (e.g., gefitinib) have attract attention, and the molecular targeting drugs having the anti-tumor effect have been developed. A method for identifying an oncogene that is promising as a novel molecule to be targeted is utilized in the development of such molecular targeting drugs. An example of such a method for identifying the oncogene is a method in which a gene library anticipated to include an oncogene is introduced into a cell and a gene introduced into the cell, which exhibits a transformation capacity, is selected as the oncogene (hereinafter a conventional identification method 1). For example, Non-patent Literature 1 discloses that a novel oncogene EML4-ALK was found by a transformation experiment utilizing a murine 3T3 cell (non-cancer cell).

Another example of the method for identifying the oncogene is a method in which gene expression is entirely analyzed between cancer cell or cancer tissue samples and normal cell or normal tissue samples using DNA chips or two dimensional electrophoresis and the oncogene is selected from the genes, expressions of which are different between the samples (hereinafter, conventional identification method 2).

(2) Establishment of Oncogene-Expressing Cell

A method for establishing an oncogene-expressing cell may include a method of isolating a cell line naturally expressing an oncogene from a subject as well as a method of introducing an oncogene together with a drug resistant gene (e.g., G418 resistant gene) into a cell and then selecting the cell carrying the oncogene using the drug (e.g., G418).

Patent Document 1 discloses that a cell line capable of proliferating in the presence of a ligand or a ligand-like substance and a drug corresponding to a drug resistant gene can be established by introducing a ligand receptor gene and the drug resistant gene into a cytokine dependent cell line (non-cancer cell), although the establishment of the oncogene-expressing cell is not focused.

(3) Screening for Oncogene Targeting Drug

An example of a method for screening an oncogene targeting drug using a cell is a method of using a cancer cell line naturally expressing an oncogene (hereinafter, conventional screening method 1).

Another example of the method for screening the oncogene targeting drug using the cell is a method of using a cell in which an oncogene has been introduced (hereinafter, conventional screening method 2). For example, Non-patent Literature 1 discloses that the EML4-ALK gene was introduced into a murine IL-3 dependent cell line (non-cancer cell line, Ba/F3 cell line) and effects of a molecular targeting drug that targeted the EML4-ALK gene was verified.

Patent Document 1 discloses that the ligand or the ligand-like substance can be screened by using the aforementioned cell line derived from the cytokine dependent cell line (non-cancer cell line), although the screening for the oncogene targeting drug is not focused.

PRIOR ART LITERATURE

Patent Literature

Patent Document 1: International Publication WO2003/012087

Non-Patent Literature

Non-patent Literature 1: Nature, vol. 448, p. 561-566 (2007).

SUMMARY OF INVENTION

Problem to be Solved by the Invention

However, the conventional techniques have the following problematic points when utilized in the research and development of the anti-cancer drugs.

(1) Identification of Oncogene

The conventional identification method 1 is carried out by directly examining a transformation capacity as an oncogene. Thus, it is highly likely that a gene identified by this method is an oncogene. However, this method is problematic in practical application and general versatility to human. Only fibroblast derived from a rodent animal is generally used as a normal cultured cell used in this method. No experimental method using a cell derived from a human and a cancer cell, or an epithelial cell and a blood cell that is an origin of many cancers is established. It is also difficult that the fibroblast derived from the rodent animal, which is used for the conventional identification method 1, is passaged for a long period of time with keeping an original nature. Such a fibroblast also has a risk that naturally occurring transformation during the passage makes it difficult to identify an objective oncogene.

The conventional identification method 2 is problematic in that many genes which are induced or suppressed by the expression of the oncogene are selected as candidate genes in addition to the oncogene. The conventional identification method 2 also requires to further analyze many candidate genes in detail for the purpose of finally identifying the oncogene from the selected many candidate genes.

(2) Establishment of Oncogene-Expressing Cell Line

The conventional establishment methods are inefficient because the oncogene can not be introduced into the cancer cell in many cases and the once introduced oncogene can be deleted via the passage.

(3) Screening for Oncogene Targeting Drug

The conventional screening method 1 can be carried out when a particular cancer cell line that naturally expresses a particular oncogene is available. However, it is difficult to obtain various cancer cell lines that naturally express any oncogene. Thus, it is not practically possible to screen targeting drugs for any oncogene.

The conventional screening method 2 can verify the effect of an inhibitor of the known oncogene using a cultured cell line usually used. However, this method is also problematic in identification of the oncogene and establishment of the oncogene-expressing cell line as described above. Thus, it is still difficult to efficiently verify the effect of the inhibitors of various oncogenes using various cultured cell lines (e.g., human cells, cancer cells).

Therefore, it is an object of the present invention to provide novel methodologies capable of solving these problematic points in the identification of the oncogene, the establishment of the oncogene-expressing cell line, and the screening for the oncogene targeting drug.

Means for Solving Problem

Oncogene addiction or addition refers to a state where a cancer cell proliferates depending on a particular gene. It is known that the proliferation of the cancer cell which proliferates depending on the particular gene can be inhibited by treating such cancer cell with an inhibitor of such a gene.

As a result of an extensive study, the present inventors have found that dependence on a particular oncogene in a cancer cell can be replaced by introducing another oncogene. The present inventors also have found based on this finding that an artificial cell which proliferates selectively is obtained by a methodology of treating a cancer cell with an expression vector for a foreign oncogene and then culturing the cancer cell treated with the expression vector under a condition which inhibits an expression or a function of an oncogene which is inherent to the cancer cell, and that this selectively proliferating artificial cell can be used as a cancer cell model. The present inventors also have found that an oncogene can be identified by utilizing this methodology and that an anti-cancer drug can be developed by utilizing the selectively proliferating cancer cell obtained by this methodology, and completed the present invention. Patent Document 1 and Non-patent Literature 1 neither describe nor suggest that the cancer cell is utilized as the cell for introducing the oncogene and the cancer cell in which the oncogene has been introduced is selected by culturing the cell under the condition which inhibits the oncogene which is inherent to the cancer cell.

Accordingly, the present invension is as follows:

[1] An artificial cell having the following properties (a) and (b):
(a) the cell is derived from a cancer cell; and
(b) the cell expresses a foreign oncogene, and has an ability to proliferate depending on the foreign oncogene.

[2] The artificial cell of [1], further having the following property (c):
(c) which retains an ability to express an oncogene that is inherent to said cancer cell, and an ability to proliferate depending on the inherent oncogene.

[3] The artificial cell of [1] or [2], wherein the artificial cell is a cell line.

[4] The artificial cell of any one of [1]-[3], wherein the artificial cell is derived from human.

[5] The artificial cell of any one of [1]-[4], wherein the artificial cell is an adherent cell.

[6] The artificial cell of any one of [1]-[5], wherein the artificial cell is derived from a lung.

[7] The artificial cell of any one of [2]-[6], wherein the inherent oncogene is an inherent tyrosine kinase gene.

[8] The artificial cell of [7], wherein the inherent tyrosine kinase gene is a mutated EGFR gene.

[9] The artificial cell of any one of [1]-[8], wherein the foreign oncogene is a foreign tyrosine kinase gene.

[10] The artificial cell of [9], wherein the foreign tyrosine kinase gene is an EML4-ALK gene.

[11] A method for establishing an artificial cell, comprising the following steps (a) to (c):

(a) a step of treating a cancer cell with an expression vector for a foreign oncogene;
(b) a step of culturing the cancer cell treated with said expression vector under a condition which inhibits an expression or function of an oncogene that is inherent to said cancer cell; and
(c) a step of obtaining a cancer cell which proliferates in step (b), as an artificial cell which expresses a foreign oncogene, and has an ability to proliferate depending on the foreign oncogene.

[12] The method of [11], further comprising the following step (d):
(d) a step of cloning the artificial cell obtained in the step (c).

[13] A method of screening a substance having an anti-cancer activity, comprising the following steps (a) and (b):
(a) a step of evaluating whether or not a test substance inhibits a proliferation of the artificial cell of any one of [1]-[10]; and
(b) a step of selecting a test substance that inhibits the proliferation of the artificial cell as the substance having the anti-cancer activity.

[14] The method of [13], wherein the step (a) is carried out under a condition that inhibits an expression or function of the inherent oncogene.

[15] A method for identifying an oncogene, comprising the following steps (a) to (c):
(a) a step of treating a cancer cell with an expression vector for a test gene;
(b) a step of culturing the cancer cell treated with said expression vector under a condition which inhibits an expression or function of an oncogene that is inherent to said cancer cell; and
(c) a step of confirming whether or not the cancer cell cultured in the step (b) proliferates depending on the test gene.

[16] The method of [15], wherein the test gene is a single gene.

[17] The method of [15], wherein the test gene is a plurality of genes, and the method further comprises the following steps:
(d) a step of cloning an cancer cell that proliferates in the step (c); and
(e) a step of identifying a test gene that is introduced into the cloned cancer cell as an the oncogene.

[18] The method of [15], wherein the test gene is a plurality of genes, and the method further comprises the following steps:
(f) a step of obtaining a test gene that is introduced into the cancer cell that proliferates in the step (c) from the cancer cell; and
(g) a step of cloning the obtained test gene for identifying the obtained test gene as an the oncogene.

Effect of the Invention

The artificial cell of the present invention enables to, for example, develop an excellent anti-cancer drug for various cancers.

The establishment method of the present invention is excellent in, for example efficiency for establishing the cell expressing the foreign oncogene.

The screening method of the present invention enables to, for example, develop the anti-cancer drug using any cancer cell expressing any oncogene.

The identification method of the present invention is excellent in, for example, sensitivity and accuracy in oncogene identification because its methodology is the same as in the establishment method of the present invention that is excellent in efficiency for establishing the cell expressing the foreign oncogene.

These methods of the present invention also have the advantage that they can be performed by convenient and routine techniques using cultured cells (e.g., cancer cell lines) usually used.

Figure 1:
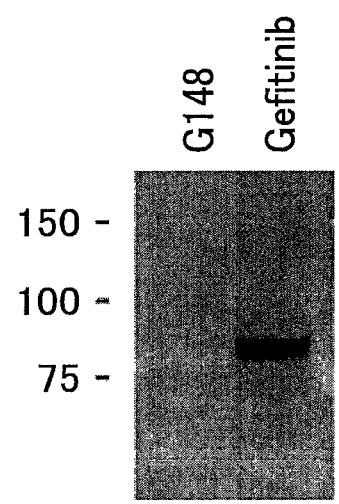
FIG. 1 is a view showing an expression of an EML4-ALK variant 3a protein in PC-9 cells transfected with an EML4-ALK variant 3a gene and proliferated in G418-containing medium (G418) or gefitinib-containing medium (Gefitinib)

BEST MODES FOR CARRYING OUT THE INVENTION (1. Artificial Cell)

The present invention provides a particular artificial cell. The term "artificial cell" as used herein means an artificially produced cell.

The artificial cell of the present invention may be an isolated or purified cell. The cell can be isolated or purified by a publicly known method such as FACS.

The artificial cell of the present invention can be derived from a cancer cell. Therefore, the artificial cell of the present invention can take over cytological properties possessed by the cancer cell. For example, when the cancer cell is a human cell, the artificial cell of the present invention can be the human cell. When the cancer cell is a lung cell, the artificial cell of the present invention can be the lung cell.

The term "cancer cell" as used herein means a tumor cell having an ability to proliferate depending on a particular oncogene expressed in the cancer cell. The cancer cell may include a primary cultured cell, a cell line, or a cancer stem cell.

As used herein, the "dependence (depending)" concerning the proliferation of the cell refers to the state of the oncogene addiction or the addiction, where the cell proliferates depending on the particular oncogene. Whether or not the cell proliferates depending on the particular oncogene can be confirmed by treating the cell with an inhibitor of the particular oncogene and then evaluating a proliferation ability of the treated cell. The proliferation ability can be evaluated by, for example, an MTT assay or an MTS assay. It is known that cell death due to apoptosis can be induced, when the cell in the oncogene addiction for the particular oncogene is treated with the inhibitor of such an oncogene. Therefore, the oncogene addiction in the cell for the particular oncogene may be confirmed by evaluating whether or not the apoptosis can be induced by inhibition of the oncogene. The induction of the apoptosis can be evaluated by, for example, a TUNEL assay, detection of active caspase, or detection of annexin V.

The cancer cell can be derived from any tissues. Examples of such a tissue may include respiratory tissues (e.g., lung, trachea, bronchi, pharynx, nasal cavity, paranasal cavity), gastrointestinal tissues (e.g., stomach, small intestine, large intestine, rectum), pancreas, kidney, liver, thymus, spleen, heart, thyroid, adrenal, prostate, ovary, uterus, brain, skin, and a blood tissue (e.g., bone marrow, peripheral blood). In another viewpoint, the cancer cell can be an adherent cell or a non-adherent cell (i.e., a blood cell), and the adherent cell is preferable. In still another viewpoint, the cancer cell can be a cell present in the above tissues or tissues other than the above tissues. Examples of such a cell may include a gland cell (e.g., gland cell (adenocyte) in lung, mammary gland cell), an epithelial cell, an endothelial cell, an epidermal cell, an interstitial cell, a fibroblast, an adipocyte, a mesangium cell, a pancreatic β cell, a nerve cell, a glia cell, and a blood cell. The cancer cell is preferably a lung adenocarcinoma cell.

The term "cancer" as used herein refers to any malignant tumor in the aforementioned tissue and cell type. Examples of the cancer may include a cancer which can be caused by an abnormal adherent cell, and a cancer which can be caused by an abnormal blood cell (e.g., leukemia, lymphoma, multiple myeloma), and the cancer caused by the abnormal adherent cell is preferable. Specifically, examples of the cancer which can be caused by the abnormal adherent cell may include a lung cancer (e.g. squamous cell carcinoma, non-small cell carcinoma such as adenocarcinoma and large cell carcinoma, and small cell carcinoma), a gastrointestinal cancer (e.g., stomach cancer, small intestine cancer, large intestine cancer, rectal cancer), a pancreatic cancer, a renal cancer, a hepatic cancer, a thymic cancer, a spleen cancer, a thyroid cancer, an adrenal cancer, a prostate cancer, an urinary bladder cancer, an ovarian cancer, an uterus cancer (e.g., endometrial carcinoma, cervical cancer), a bone cancer, a skin cancer, a brain tumor, a sarcoma, a melanoma, a blastoma (e.g., neuroblastoma), an adenocarcinoma, a planocellular cancer, a solid cancer, an epithelial cancer, and a mesothelioma. The "cancer" in cancer-related terms such as terms "cancer cell" and "cancer gene (oncogene)" can also mean the same meaning.

The cancer cell can be derived from any mammalian species. Such a mammalian species may include, for example, humans, monkeys, cattle, swines, mice, rats, guinea pigs, hamsters, and rabbits. The mammalian species is preferably the human in terms of clinical application. Therefore, the cancer cell may be a cancer cell isolated from a patient with cancer or a cancer cell derived therefrom.

The cancer cell may be a cell not infected with virus or a cell infected with virus. Examples of a carcinogenic virus capable of infecting the cell may include Epstein Barr virus, hepatitis virus, human papilloma virus, human T cell leukemia virus, and Kaposi sarcoma-associated herpes virus. The cancer cell may also be a cancer cell derived from an embryonic stem cell, a somatic stem cell, or an artificial stem cell (e.g., iPS cell) produced from a normal cell.

The cancer cell from which the artificial cell of the present invention is derived can express an inherent oncogene. As used herein, the term "inherent oncogene" means an oncogene responsible for proliferation of the cancer cell, which is expressed by the cancer cell that can be used as a material in the establishment of the artificial cell of the present invention. The oncogene can be a gene that is overexpressed in the cancer cell (e.g., overexpression due to increase of copy number of the gene) and transmits a signal for proliferation excessively, or a gene that a mutation occurs which continuously transmit a proliferation signal in the cancer cell. Examples of the mutation may include point mutation (e.g., substitution), deletion, addition, insertion, and mutation causing a fusion (e.g., inversion, translocation). As used herein, the term "gene" may intend to be a mutated gene.

The term "inherent" as used herein means a concept opposed to the term "foreign". Therefore, when a gene is introduced into a cancer cell in a process of establishing the artificial cell of the present invention using the cancer cell as a material, the gene is foreign for the cancer cell. Meanwhile, a gene possessed by the cancer cell which can be used as the material in the process for establishing the artificial cell of the present invention is meant to be inherent to the cancer cell even if the gene is introduced or mutated in a process for establishing the cancer cell.

Examples of the inherent oncogene may include oncogenes derived from the mammalian or the virus. Examples of the mammalian species may include humans, monkeys, cattle, swines, mice, rats, guinea pigs, hamsters, and rabbits. The mammalian species is preferably the human in terms of clinical application. Examples of the virus may include Epstein Barr virus, hepatitis virus, human papilloma virus, human T cell leukemia virus, and Kaposi sarcoma-associated herpes virus.

Examples of the inherent oncogene may include genes for kinase such as tyrosine kinase (receptor type, and non-receptor type) and serine/threonine kinase, small G-proteins, and transcription factors, and the tyrosine kinase gene is preferable. Examples of the tyrosine kinase which can play a role in proliferation of the cancer cell may include molecules belonging to an epidermal growth factor receptor (EGFR) family (e.g., EGFR, HER2, HER3, HERO), molecules belonging to platelet derived growth factor receptor (PDGFR) family (e.g., PDGFRα, PDGFRβ), an anaplastic lymphoma kinase (ALK), a hepatocyte growth factor receptor (c-MET), and a stem cell factor receptor (c-KIT).

In one embodiment, the inherent oncogene can be an oncogene capable of transmitting a proliferation signal in a signaling pathway of the molecules belonging to the EGFR family (e.g., EGFR, HER2, HER3, HER4). Examples of such an oncogene may include EGFR, HER2, HER3, HER4, RAS, RAF, MYC, AKT, MAP kinase, PI3 kinase, and PKC genes.

In another embodiment, the inherent oncogene can be an oncogene capable of transmitting a proliferation signal in a signaling pathway of the molecules belonging to PDGFR family (e.g., PDGFRα, PDGFRβ). Examples of such an oncogene may include PDGFRα, PDGFRβ, RAS, RAF, MYC, AKT, MAP kinase, PI3 kinase, and PKC genes.

In still another embodiment, the inherent oncogene can be an oncogene capable of transmitting a proliferation signal in a signaling pathway of the ALK gene (e.g., mutated ALK gene described later). Examples of such an oncogene may include RAS, MAP kinase, AKT, PI3 kinase, and STATS genes.

The inherent oncogene may be an oncogene of types described in the foreign oncogene described later.

The cancer cell from which the artificial cell of the present invention is derived can have an ability to proliferate depending on an(the) inherent oncogene. As used herein, the term "ability to proliferate depending on the inherent oncogene" means that the cancer cell expressing the inherent oncogene can proliferate by the proliferation signal due to the inherent oncogene. Therefore, the cancer cell expressing the inherent oncogene can not proliferate depending on the inherent oncogene when the expression or function of the inherent oncogene is inhibited. Whether or not the cancer cell proliferates depending on the inherent oncogene can be confirmed by evaluating whether or not a proliferation ability of the cancer cell can be reduced under a condition which inhibits the expression or function of the inherent oncogene (e.g., in the presence of the inhibitor of the inherent oncogene).

The inhibition of the function of the inherent oncogene in the cancer cell can be accomplished by, for example, the inhibitor or gene disruption of the inherent oncogene. As used herein, the term "inhibitor of an(the) inherent oncogene" means a substance capable of inhibiting the proliferation of the cancer cell by inhibiting an expression or function of mRNA or a protein from the aforementioned inherent oncogene.

In one embodiment, examples of the inhibitor of the inherent oncogene may include antisense nucleic acids for mRNA expressed from the inherent oncogene (e.g., DNA, RNA, and artificial nucleic acids such as PNA), RNA interference inducible nucleic acids (e.g., siRNA: either double stranded RNA or single stranded RNA having a stem loop structure) and aptamers, and antibodies against the protein expressed from the inherent oncogene (e.g., polyclonal antibodies, monoclonal antibodies, chimera antibodies, humanized antibodies, human antibodies, single stranded antibodies such as scFv), and expression vectors therefor. The inhibitor of the inherent oncogene can be a small compound. The inhibitor of the inherent oncogene may also be a substance that inhibits cell proliferation by cell death due to apoptosis. The disruption of the inherent oncogene can be carried out by a targeting vector for the inherent oncogene. Those skilled in the art can easily make such an inhibitor and disrupt the gene by obtaining information of the target gene (e.g., sequence information).

In another embodiment, the inhibitor of the inherent oncogene is a molecular targeting drug that targets the oncogene. Examples of the molecular targeting drug are known for the followings:
1) Gefitinib, erlotinib, and cetuximab for the epidermal growth factor receptor (EGFR);
2) Trastuzmab for HER2
3) Imatinib for BCR-ABL fusion protein, c-KIT, and PDGFRα;
4) PHA-66575 and SU-11274 for c-MET (see, e.g., Science (2007): vol. 316, p. 1039-1043; and Cancer Research (2005): vol. 65, p. 1479-1488); and
5) NVP-TAE684 and PF-02341066 for ALK (see, e.g., PNAS (2007): vol. 104, p. 270-275; and Molecular Cancer Therapy (2007): vol. 6, p. 3314-3322).

The cancer cell from which the artificial cell of the present invention is derived is preferably a cancer cell that expresses an oncogene which can be targeted by an existing molecular targeting drug as the inherent oncogene because the artificial cell of the present invention is easily established by utilizing the existing cancer cell and the existing molecular targeting drug. Examples of such a cancer cell may include an EGFR gene expressing cell, an HER2 gene expressing cell, a BCR/ABL fusion gene expressing cell, an EML4-ALK gene expressing cell, a PDGFRα gene expressing cell, and a c-MET gene expressing cell. Examples of the EGFR gene expressing cell may include PC-9 cell (derived from human non-small cell lung cancer), HCC827 cell (derived from human non-small cell lung cancer), and HCC4006 cell (derived from human non-small cell lung cancer). Examples of the HER2 gene expressing cell may include NCI-H2170 (derived from human non-small cell lung cancer), BT474 (derived from human breast cancer), HCC1419 (derived from human breast cancer), and MDA-MB-361 (derived from human breast cancer). Examples of the BCR/ABL fusion gene expressing cell may include K562 (derived from human leukemia), KCL22 (derived from human leukemia), KU812 (derived from human leukemia), and AR230 (derived from human leukemia). Examples of the PDGFRα gene expressing cell may include NCI-H1703 (derived from human non-small cell lung cancer). Examples of the EML4-ALK gene expressing cell may include NCI-H2228 (derived from human non-small cell lung cancer), NCI-H3122 (derived from human non-small cell lung cancer), and DFC1032 (derived from human non-small cell lung cancer). Examples of the c-MET gene expressing cell may include NCI-H1993 (derived from human non-small cell lung cancer), NCI-H820 (derived from human non-small cell lung cancer), and MKN45 (derived from human stomach cancer).

The artificial cell of the present invention can also express a foreign oncogene. As used herein, the term "foreign oncogene" means an oncogene that is introduced into the cancer cell in the process for establishing the artificial cell of the present invention using the aforementioned cancer cell as the material. The kind of the foreign oncogene is an oncogene different from that of the inherent oncogene. The foreign oncogene may be a single gene or a plurality of genes. As used herein, the term "foreign" means the concept opposed to the term "inherent" as described above.

Examples of the foreign oncogene may include oncogenes derived from the mammalians. Examples of the mammalian species may include humans, monkeys, cattle, swines, mice, rats, guinea pigs, hamsters, and rabbits. The mammalian species is preferably the human in terms of clinical application.

Examples of the foreign oncogene may include kinase genes such as tyrosine kinase (receptor type, and non-receptor type) and serine/threonine kinase genes, small G-protein genes, and transcription factor genes, and the tyrosine kinase gene is preferable. The tyrosine kinases capable of playing a role in the proliferation of the cancer cell are the same as those aforementioned in the inherent oncogene.

In one embodiment, the foreign oncogene can be the oncogene capable of transmitting the proliferation signal in the signaling pathway of the molecule belonging to the EGFR gene family. Such oncogenes are the same as those aforementioned in the inherent oncogene.

In another embodiment, the foreign oncogene can be the oncogene capable of transmitting the proliferation signal in the signaling pathway of the molecule belonging to the PDGFR gene family. Such oncogenes are the same as those aforementioned in the inherent oncogene.

In still another embodiment, the inherent oncogene can be the oncogene capable of transmitting the proliferation signal in the signaling pathway of an ALK gene (e.g., an mutated ALK gene such as EML4-ALK described later). Such oncogenes are the same as those aforementioned in the inherent oncogene.

In certain embodiments, the foreign oncogene can be the mutated PDGFRα gene or the mutated ALK gene. Examples of such a mutated gene may include the genes that the mutation described above occurs. Representative examples of the mutated PDGFRα gene that is the oncogene may include genes having a point mutation in the PDGFRα gene (e.g., V561D, D842V). Representative examples of the mutated ALK gene that is the oncogene may include ALK fusion genes and genes having the point mutation in the ALK gene. Examples of the ALK fusion gene may include an EML4-ALK gene, an NPM-ALK gene, a TPM3-ALK gene, a TPM4-ALK gene, an ATIC-ALK gene, a TFG-ALK gene, a CLTC-ALK gene, an MSN-ALK gene, an MYH9-ALK gene, an ALO17-ALK gene, a CARS-ALK gene, an RANBD2-ALK gene, and an SFC31L1-ALK gene. Various ALK variants are known in the EML4-ALK gene. Examples of such a variant may include variant 1, variant 2, variant 3 (e.g., 3a, 3b), variant 4, variant 5 (e.g., 5a, 5b), variant 6, and variant 7 (see e.g., J. Clin. Oncol., 2009 Sep. 10; 27(26): 4232-5)

The expression of the foreign oncogene can be accomplished by introducing into a cell an artificial expression vector (e.g., plasmid, adenovirus, retrovirus) in which the foreign oncogene has been incorporated together with a promoter that induces the expression of that gene. The expression can be transient expression or constitutive (i.e., stable) expression. For example, the transient expression of the foreign oncogene can be accomplished by introducing the expression vector for the foreign oncogene into the cancer cell so as to initiate the expression of the oncogene in the cancer cell. The constitutive expression of the foreign oncogene can be accomplished by introducing the expression vector for the foreign oncogene into the cancer cell and selecting the cell in which the insert has been incorporated into the genome.

The artificial cell of the present invention can have the ability to proliferate depending on the foreign oncogene. As used herein, the term "ability to proliferate depending on a(the) foreign oncogene" concerning the artificial cell means that the artificial cell expressing the foreign oncogene can proliferate by the proliferation signal due to the foreign oncogene. Therefore, when the artificial cell expressing the foreign oncogene further expresses the inherent oncogene, it can proliferate depending on the foreign oncogene even if the expression or function of the inherent oncogene is inhibited. Whether or not the artificial cell proliferates depending on the foreign oncogene can be confirmed by, for example, evaluating whether or not the proliferation ability of the artificial cell is reduced under a condition which inhibits an expression or function of the foreign oncogene. In addition, whether or not the artificial cell proliferates depending on the foreign oncogene can be confirmed by evaluating whether or not the proliferation ability of the artificial cell can be retained under a condition which inhibits the inherent oncogene.

The inhibition of the function of the foreign oncogene in the artificial cell can be accomplished by an inhibitor of the foreign oncogene. As used herein, the term "inhibitor of a(the) foreign oncogene" means the substance capable of inhibiting the proliferation of the cancer cell described above by inhibiting the expression or function of mRNA or the protein from the aforementioned foreign oncogene.

In one embodiment, examples of the inhibitor of the foreign oncogene may include antisense nucleic acids for mRNA expressed from the foreign oncogene (e.g., DNA, RNA, and artificial nucleic acids such as PNA), RNA interference inducible nucleic acids (e.g., siRNA: either double stranded RNA or single stranded RNA having a stem loop structure) and aptamers, and antibodies against the protein expressed from the foreign oncogene (e.g., polyclonal antibodies, monoclonal antibodies, chimera antibodies, humanized antibodies, human antibodies, single stranded antibodies such as scFv), and expression vectors therefor. The inhibitor of the foreign oncogene can be a small compound. The inhibitor of the foreign oncogene may also be the substance that inhibits the cell proliferation by the cell death due to the apoptosis. Those skilled in the art can easily make such an inhibitor by obtaining the information of the target gene (e.g., sequence information).

In another embodiment, the inhibitor of the foreign oncogene is a molecular targeting drug that targets an oncogene. Examples of the molecular targeting drug may include those described in the inhibitor of the inherent oncogene described above.

The artificial cell of the present invention can retain an ability to express the oncogene that is inherent to the cancer cell and an ability to proliferate depending on the inherent oncogene (an ability of the cancer cell which can be utilized for establishing the artificial cell). As used herein, the term "ability to proliferate depending on an(the) inherent oncogene" concerning the artificial cell means that the artificial cell expressing the foreign oncogene and the inherent oncogene can proliferate by the proliferation signal due to the inherent oncogene. Therefore, the artificial cell expressing the foreign oncogene and the inherent oncogene can proliferate depending on the inherent oncogene even when the expression or function of the foreign oncogene is inhibited. Whether or not the artificial cell proliferates depending on the inherent oncogene can be confirmed by, for example, evaluating whether or not the proliferation ability of the artificial cell can be reduced under a condition which inhibits the expression or function of the inherent oncogene. In addition, whether or not the artificial cell proliferates depending on the inherent oncogene can be confirmed by evaluating whether or not the proliferation ability of the artificial cell can be retained under a condition which inhibits the foreign oncogene.

It can be desired that the artificial cell of the present invention further mimics the natural cancer cell. Therefore, the cancer cell, the inherent oncogene, and the foreign oncogene may be derived from the same mammalian species. The cancer cell, the inherent oncogene, and the foreign oncogene are preferably derived from the human in terms of clinical application. However, the oncogene is derived from the virus in some cases. Thus, the inherent oncogene and/or the foreign oncogene may be derived from the virus.

The artificial cell of the present invention may express one or more other foreign genes in addition to the foreign oncogene. Such a foreign gene may include activation factors of the foreign oncogenes (e.g., secretory proteins such as EGF, PDGF, and HGF).

The artificial cell of the present invention can be characterized by following (A) and (B).

(A) An artificial cell expressing the foreign oncogene and the inherent oncogene:

(A1) an artificial cell transiently expressing the foreign oncogene and expressing the inherent oncogene (e.g., a cancer cell transfected with the expression vector for the foreign oncogene); and (A2) an artificial cell constitutively expressing the foreign oncogene and expressing the inherent oncogene (e.g., a cancer cell incorporating the foreign oncogene into the genome)

(B) An artificial cell expressing the foreign oncogene and incapable of expressing the inherent oncogene:

(B1) an artificial cell which transiently expresses the foreign oncogene and can not transiently express the inherent oncogene (e.g., a cancer cell transfected with the expression vector for the foreign oncogene, which is treated with the inhibitor of the inherent oncogene);

(B2) an artificial cell which transiently expresses the foreign oncogene and can not constitutively express the inherent oncogene (e.g., a cancer cell transfected with the expression vector for the foreign oncogene, in which the inherent oncogene is disrupted);

(B3) an artificial cell which constitutively expresses the foreign oncogene and can not transiently express the inherent oncogene (e.g., a cancer cell incorporating the foreign oncogene into the genome, which is treated with the inhibitor of the inherent oncogene); and (B4) an artificial cell which constitutively expresses the foreign oncogene and can not constitutively express the inherent oncogene (e.g., a cancer cell incorporating the foreign oncogene into the genome, in which the inherent oncogene is disrupted).

(2. Method for Establishing Artificial Cell)

The present invention provides a method for establishing (i.e., method for producing) the artificial cell of the present invention. The establishment method of the present invention can comprise the following steps (a) to (c):

(a) a step of treating a cancer cell with an expression vector for a foreign oncogene;

(b) a step of culturing the cancer cell treated with the expression vector under a condition which inhibits an expression or function of an oncogene that is inherent to the cancer cell; and (c) a step of obtaining the cancer cell which proliferates in the step (b), as an artificial cell which expresses a foreign oncogene, and has an ability to proliferate depending on the foreign oncogene.

In the step (a) in the establishment method, the expression vector for the foreign oncogene can be introduced into the cancer cell by treating the cancer cell with the expression vector for the foreign oncogene in a culture medium. Examples of the treatment for introducing the expression vector into the cancer cell may include an electroporation method, a calcium phosphate method, and a liposome method.

The culture medium can be prepared using a medium used for culturing a mammalian cell as a basic medium. Examples of the basic medium may include MEM medium, DMEM medium, αMEM medium, HAM medium, RPMI 1640 medium, Fischer's medium, and mixed media thereof. The culture medium can contain, for example, serum (e.g., FCS), serum replacement (e.g., KSR), fatty acids or lipids, amino acids, vitamins, cytokines, antioxidants, 2-mercaptoethanol, pyruvic acid, buffer, inorganic salts, and the like. Conditions such as the number of cells and concentrations of various factors in the cultivation can be determined appropriately.

The cancer cell can be obtained by publicly known methods. For example, the cancer cell can be isolated from the mammalian species suffered from the cancer, and may be obtained by establishing a cell line after the isolation. The existing cell line can also be utilized as the cancer cell. Those skilled in the art can identify an oncogene that is inherent to the obtained cancer cell, and can easily determine whether or not the cancer cell has an ability to proliferate depending on a cell growth factor gene that is inherent to the cancer cell.

A promoter used in the expression vector is not particularly limited as long as the promoter can work in a cell to which the promoter is introduced, and examples thereof may include virus promoters (e.g., an SV40 derived early promoter, cytomegalovirus LTR, Rous sarcoma LTR, MoMuLV derived LTR, adenovirus derived early promoter), structural gene promoters derived from the mammalians (e.g., β-actin gene promoter, PGK gene promoter, transferrin gene promoter).

The expression vector preferably comprises a transcription termination signal (i.e., terminator region) downstream of an oligo(poly)nucleotide encoding a nucleic acid molecule. Further, the expression vector may comprise a gene resistant to a drug (e.g., G418), but such a drug-resistant gene is essentially unnecessary in the establishment method of the present invention, and thus, such a resistant gene need not be included.

A basic vector of the expression vector used for introducing the foreign gene into the cancer cell can be, for example, plasmids or virus vectors (e.g., vectors derived from viruses such as adenovirus, retrovirus, adeno-associated virus, herpes virus, vaccinia virus, poxvirus, poliovirus, sindbis virus, Sendai virus and lentivirus).

In the step (b) in the establishment method, the cancer cell that has acquired the dependency on the introduced foreign oncogene can proliferate selectively by culturing the cancer cell treated with the expression vector in the step (a) under the condition which inhibits the expression or function of the inherent oncogene. The condition which inhibits the expression or function of the inherent oncogene can be accomplished by culturing in the presence of the inhibitor of the inherent oncogene (and in the absence of the inhibitor of the foreign oncogene). Even when the expression vector contains a gene resistant to a particular drug, this step can be carried out in the absence of the drug. A culture temperature is, for example, about 30 to 40° C. and preferably about 37° C. A $CO_2$ concentration is, for example, about 1 to 10% and preferably about 5%.

In the step (c) in the establishment method, the artificial cell which expresses the foreign oncogene and has the ability to proliferate depending on the foreign oncogene is obtained by collecting the cell which has proliferated in the step (b).

The establishment method of the present invention may further comprise a step of cloning the artificial cell obtained in the step (c) in order to establish a cell line of the artificial cell. The cloning of the artificial cell can be carried out by publicly known methods such as a limiting dilution method.

The establishment method of the present invention may further comprise a step of confirming the expression of the foreign oncogene in the artificial cell and/or a step of confirming the ability to proliferate depending on the foreign oncogene in the artificial cell. Such a step can be carried out in the same manner as in the aforementioned method of evaluating whether or not the cancer cell proliferates depending on the foreign oncogene.

The establishment method of the present invention may also comprise a step of confirming whether or not the artificial cell retains the ability to proliferate depending on the inherent oncogene. Such a step can be carried out in the same manner as in the aforementioned method of evaluating whether or not the cancer cell proliferates depending on the inherent oncogene.

The establishment method of the present invention may further comprise a step of treating the cancer cell that has acquired the dependency on the introduced foreign oncogene with the inhibitor of the inherent oncogene in order to establish the artificial cell as in (B1) and (B3) above. The establishment method of the present invention may further comprise a step of disrupting the inherent oncogene in the cancer cell that has acquired the dependency on the introduced foreign oncogene in order to establish the artificial cell as in (B2) and (B4) above. The cancer cell that has acquired the dependency on the introduced foreign oncogene can proliferate without requiring the inherent oncogene. The inherent oncogene can be disrupted by utilizing a gene knockout technology using a targeting vector for the gene. The artificial cell in which the inherent oncogene has been disrupted is useful for developing a substance having an anti-cancer activity specific for the foreign oncogene.

The establishment method of the present invention may also comprise a step of providing a cancer cell to be used in the step (a). The step of providing the cancer cell may comprise obtaining the cancer cell, then identifying the inherent oncogene expressed in the cancer cell, and confirming whether or not the cancer cell proliferates depending on the identified inherent oncogene. Meanwhile, when it has been already demonstrated that the obtained cell has such a property (e.g., the obtained cell is the characterized cancer cell), the step of providing the cancer cell may comprise only obtaining the cancer cell. The cancer cell can be isolated from the mammalian species suffered from the cancer, and may be obtained by establishing a cell line after the isolation. The existing cell line can also be utilized as the cancer cell.

(3. Method of Screening Substance Having Anti-Cancer Activity

The present invention provides a method of screening a substance having an anti-cancer activity. The screening method of the present invention can comprise the following steps (a) and (b):

(a) a step of evaluating whether or not a test substance inhibits a proliferation of the artificial cell; and (b) a step of selecting the test substance that inhibits the proliferation of the artificial cell as the substance having the anti-cancer activity.

In the step (a) in the screening method, the evaluation can be carried out by culturing the artificial cell in the presence of the test substance, and then determining whether or not the test substance inhibits the proliferation of the artificial cell. The culture medium and the culture condition are the same as those described in the establishment method of the present invention. Whether or not the test substance inhibits the proliferation of the artificial cell can be determined by comparing the number of cells cultured in the presence of the test substance with the number of cells cultured in the absence of the test substance. The determination can also be carried out by measuring an indicator of cell proliferation (e.g., activity of certain protein, amount of phosphorylated protein). The determination may also be carried out based on whether or not the test substance can induce the apoptosis.

The test substance can be any compound, and examples thereof may include a small compound, a compound library made using combinatorial chemistry technique, a nucleic acid (e.g., nucleoside, oligonucleotide, polynucleotide), a saccharide (e.g., monosaccharide, disaccharide, oligosaccharide, polysaccharide), a lipid (e.g., saturated or unsaturated straight, branched and/or cyclic fatty acid), an amino acid, a protein (e.g., oligopeptide, polypeptide), a random peptide library made by a solid phase synthesis or a phage display method, or a natural component derived from a microorganism, a plant/animal or a marine organism.

The test substance can also be a mutant of a tumor (cancer) suppressor gene. In this case, an expression vector for the mutant of the tumor suppressor gene can be introduced into the artificial cell. A mutation capable of losing a function of the tumor suppressor gene can be identified by evaluating whether or not the mutant of the tumor suppressor gene inhibits the proliferation of the artificial cell.

The step (a) may be carried out under the condition which inhibits the expression or function of the inherent oncogene. The condition which inhibits the expression or function of the inherent oncogene can be accomplished by culturing the cell in the presence of the inhibitor of the inherent oncogene. In terms of screening the substance having the anti-cancer activity specific for the foreign oncogene, it is preferable that the step (a) is carried out in the presence of the inhibitor of the inherent oncogene and in the absence of the inhibitor of the foreign oncogene. Even when the expression vector used for establishing the artificial cell of the present invention contains a drug resistant gene for a certain drug, this step can be carried out in the absence of such a drug.

In the step (b) in the screening method, the test substance that inhibits the proliferation of the artificial cell is selected as the substance having the anti-cancer activity. For example, when the number of cells cultured in the presence of the test substance is smaller than the number of cells cultured in the absence of the test substance, the test substance is selected as the substance having the anti-cancer activity. The test substance that inhibits the proliferation of the artificial cell may also be selected based on the indicator of cell proliferation (e.g., activity of certain protein, amount of phosphorylated protein) or the induction of apoptosis.

(4. Method for Identifying Oncogene)

The present invention provides a method for identifying an oncogene. The identification method of the present invention can comprise the following steps (a) to (c):

(a) a step of treating a cancer cell with an expression vector for a test gene;

(b) a step of culturing the cancer cell treated with the expression vector under a condition which inhibits the expression or function of an oncogene that is inherent to the cancer cell; and (c) a step of confirming whether or not the cancer cell cultured in the step (b) proliferates depending on the test gene.

In the step (a) in the identification method, the expression vector for the test gene can be introduced into the cancer cell by treating the aforementioned cancer cell with the expression vector for the test gene in the culture medium. Examples of the treatment for introducing the expression vector into the cancer cell may include an electroporation method, a calcium phosphate method, and a liposome method. The cancer cell, the expression vector, and the culture medium used in this step are the same as those described in the step (a) in the establishment method of the present invention.

The test gene is not particularly limited as long as it is any gene derived from the mammalian species or a pathogen (e.g., virus) that can cause the cancer. Examples of the test gene may include an overexpressed gene or a mutated gene found in the cancer cell. According to the identification method of the present invention, it can be determined that such an overexpressed gene or mutated gene is only resulted from canceration of the cancer cell or is a causal factor (i.e., oncogene) for the canceration.

The test gene can be a single gene or a plurality of genes. A gene library containing many genes may be used as a plurality of genes. An example of the gene library is a cDNA library prepared from a cultured cancer cell or prepared from a cancer tissue sample from a patient with cancer. Another example of the gene library is a cDNA library prepared from a stem cell or a germ cell or a normal cell.

In the step (b) in the identification method, the cancer cell that has acquired the dependency on the introduced test gene can proliferate selectively when the test gene is the oncogene by culturing the cancer cell treated with the expression vector in the step (a) under the condition which inhibits the expression or function of the inherent oncogene. The condition which inhibits the expression or function of the inherent oncogene can be accomplished by culturing in the presence of the inhibitor of the inherent oncogene. The culture condition is the same as that described in the step (b) in the establishment method of the present invention. Even when the expression vector capable of being involved in establishing the artificial cell of the present invention contains a drug resistant gene for a certain drug, this step can be carried out in the absence of the drug.

In the step (c) in the identification method, it is confirmed whether or not the cancer cell cultured in the step (b) proliferates depending on the test gene. Specifically, when the test gene is a single gene and the proliferation of the cancer cell is confirmed, it can be identified that the test gene is the oncogene. Also when the test gene is a plurality of genes (e.g., gene library) and the proliferation of the cancer cell is confirmed, it can be determined that the oncogene is included in the plurality of genes.

When the test gene is a plurality of genes and the proliferation of the cancer cell is confirmed, in order to identify the oncogene included in the plurality of genes, the identification method of the present invention may further comprise the following steps:

(d) a step of cloning the proliferated cancer cell; and (e) a step of identifying the test gene introduced into the cloned cancer cell as the oncogene.

In the step (d) in the identification method, the cancer cell introduced with the test gene that is the oncogene is cloned. The cloning can be carried out in the same manner as in the cloning of the artificial cell described above.

In the step (e) in the identification method, the test gene introduced into the cloned cancer cell is identified as the oncogene. For example, the test gene introduced into the cancer cell can be identified by amplifying (e.g., by PCR) DNA encoding the oncogene utilizing nucleotide sequences of flanking sites in a homologous recombinant unit (including the test gene, and flanking sites present in 5' and 3' sides to the test gene and derived from the expression vector) of the expression vector used, and then determining a nucleotide sequence of the amplified DNA. The test gene can also be identified by expression analysis using DNA chips and the like.

When the test gene is a plurality of genes, the identification method of the present invention may further comprise the following steps:

(f) a step of obtaining the test gene that is introduced into the cancer cell that proliferates in the step (c) from the cancer cell; and (g) a step of cloning the obtained test gene for identifying the obtained test gene as the oncogene.

In the step (f) in the identification method, the test gene introduced into the cancer cell is obtained as a DNA fragment from the proliferated cancer cell. For example, the test gene introduced into the cancer cell can be obtained by amplifying (e.g., by PCR) DNA encoding the oncogene using the nucleotide sequences of the flanking site in the homologous recombinant unit (including the test gene, and flanking sites present in 5' and 3' sides to the test gene and derived from the expression vector) of the expression vector used.

In the step (g) in the identification method, the obtained test gene is cloned for identifying the oncogene. The test gene can be cloned by, for example, incorporating a DNA fragment of the test gene obtained in the step (f) into a plasmid which can be replicated in *E. coli*, introducing the plasmid in which the test gene has been incorporated into *E. coli*, and then cloning *E. coli* in which the plasmid has been introduced. The oncogene can be identified by, for example, collecting the plasmid from cloned *E. coli*, amplifying (e.g., by PCR) DNA encoding the oncogene incorporated into the plasmid, and then determining the nucleotide sequence of the amplified DNA.

EXAMPLES

The present invention will be described in detail with reference to following Examples, but the present invention is not limited thereto.

Example 1

PC-9 cell (a cell line derived from human non-small cell lung cancer (pulmonary adenocarcinoma)) expresses mutated EGFR that is an oncogene. In the PC-9 cell, cell death due to apoptosis is induced by gefitinib that is an inhibitor of EGFR, resulting in inhibition of proliferation of the cell. PC-9 cells were transfected with a plasmid pcDNA3.1(−) in which another oncogene EML4-ALK variant 3a (see J Clin Oncol., 2009, Sep. 10; 27(26): 4232-5) and a G418 resistant gene had been incorporated, using transfection reagents. Subsequently, the cells transfected with the plasmid were selectively cultured in a G418-containing medium (1 mg/mL of G418) or a gefitinib-containing medium (1 µM gefitinib) prepared from RPMI 1640 medium supplemented with 10% fetal calf serum and an antibiotic kanamycin at 37° C. for three weeks. A cell extract from the cells that had proliferated in each medium was developed on SDS-PAGE, transferred onto a PVDF membrane, and subjected to western blotting using a monoclonal antibody against ALK. As a result, the expression of EML4-ALK variant 3a was not observed in the extract of cells selected in the G418-containing medium, but was observed in the extract of the cells selected in the gefitinib-containing medium (FIG. 1). These results indicate that the cell made by introducing the oncogene EML4-ALK variant 3a into the cell line PC-9 can proliferates under the condition which inhibits the oncogene (mutated EGFR that is the oncogene) that is inherent to this cell.

Example 2

Figure 2:
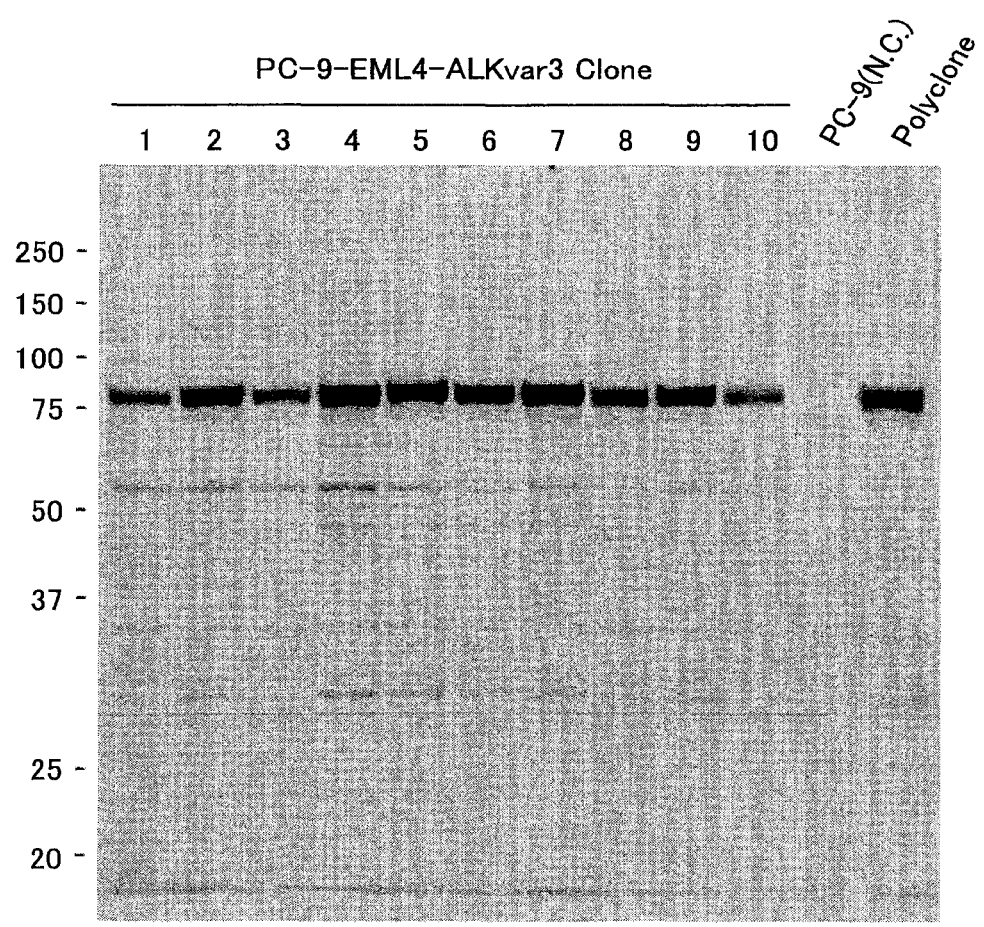
FIG. 2 is a view showing the expression of an EML4-ALK variant 3a protein in 10 clones from PC-9 cells transfected with an EML4-ALK variant 3a gene and selectively proliferated in gefitinib-containing medium.

The cells selectively proliferated in the gefitinib-containing medium in Example 1 were seeded in a 96-well plate in a limiting dilution manner. Cells proliferated as a clone in the gefitinib-containing medium were selected, and a cell extract from each clone was subjected to the western blotting using the monoclonal antibody against ALK. As a result, the expression of EML4-ALK variant 3a was confirmed in the cell extracts from all of 10 clones obtained (FIG. 2). This indicates that this methodology is very excellent in efficiency for establishing an oncogene-expressing cell.

Example 3

Figure 3:
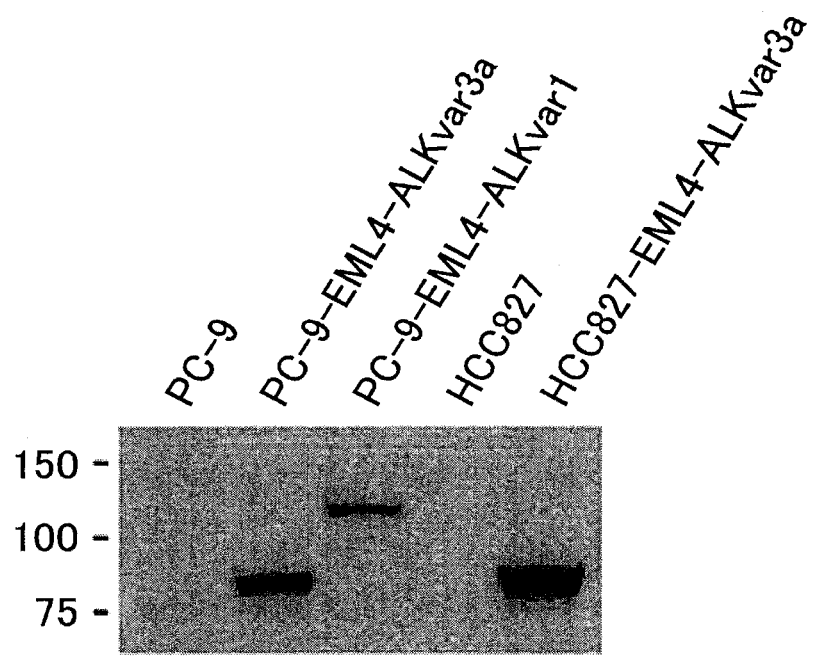
FIG. 3 is a view showing the expression of an EML4-ALK variant 3a protein or an EML4-ALK variant 1 protein in PC-9 cells transfected with an EML4-ALK variant 3a gene (PC-9-EML4-ALKvar3a), PC-9 cells transfected with an EML4-ALK variant 1 gene (PC-9-EML4-ALKvar1), and HCC827 cells transfected with the EML4-ALK variant 3a gene (HCC827-EML4-ALKvar3a), which were proliferated in gefitinib-containing medium.

The same experiment as in Example 1 was carried out using the gefitinib sensitive cell HCC827 (a cell line derived from human non-small cell lung cancer (pulmonary adenocarcinoma)) other than PC-9 cell to establish EML4-ALK variant 3a gene-introduced cells. EML4-ALK variant 1 gene (J Clin Oncol., 2009, Sep. 10; 27(26): 4232-5), another variant different from EML4-ALK variant 3a was introduced into PC-9 cells in the same manner to establish expression cells. Cell extracts were subjected to SDS-PAGE, transferred onto the PVDF membrane, and subjected to the western blotting using the anti-ALK antibody. As a result, each objective gene product was observed (FIG. 3). These results indicate that any mutated ALK gene can complement the proliferation of any cancer cell.

Example 4

Figure 4:
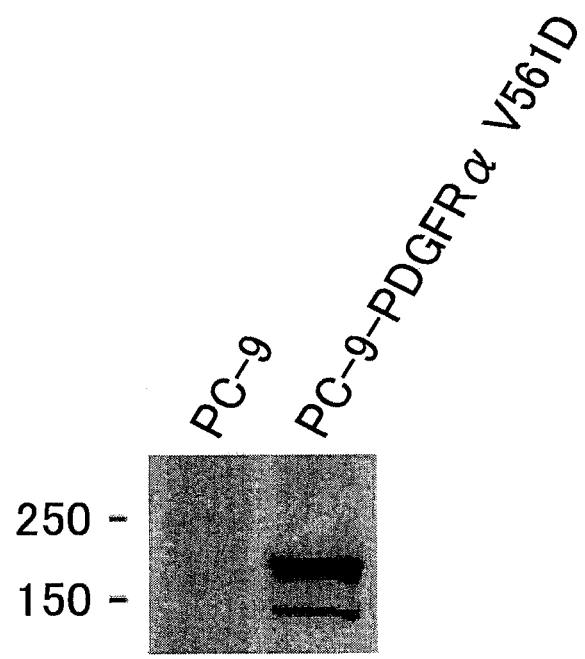
FIG. 4 is a view showing the expression of a PDGFRα V561D protein in PC-9 cells transfected with a PDGFRα V561D gene and proliferated in gefitinib-containing medium.

The same experiment as in Example 1 was carried out using the PC-9 cell to establish cells introduced with the oncogene, PDGFRα V561D gene (Science 299 (5607), 708-10 (2003)) other than the EML4-ALK gene. Cell extracts were subjected to SDS-PAGE, transferred onto the PVDF membrane, and subjected to the western blotting using an anti-PDGFRα antibody. As a result, objective gene products were observed (FIG. 4).

Example 5

Figure 5:
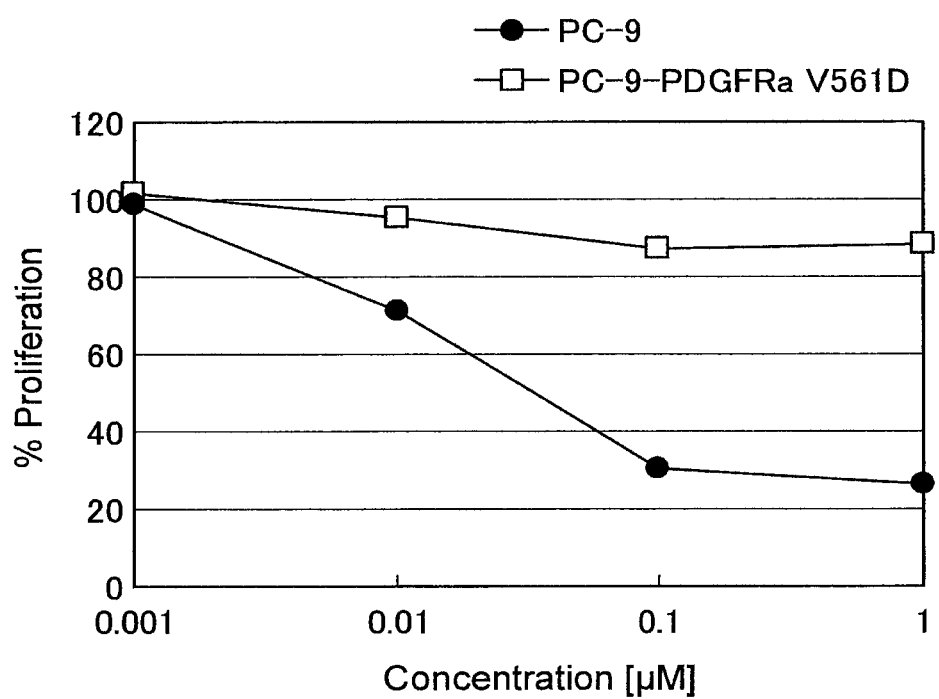
FIG. 5 is a view showing a proliferation percentage (%) of PC-9 cells or PC-9 cells transfected with the PDGFRα V561D gene in the presence of gefitinib at various concentrations.

PC-9 cells or cells obtained by introducing the oncogene, the PDGFRα V561D gene into PC-9 cells in Example 4 were seeded in a 96-well plate. The cells were cultured for 72 hours in medium containing gefitinib at various concentrations, and then living cells were quantified by an MTS assay. As a result, the proliferation of PC-9 cells was inhibited by gefitinib in a dose dependent manner, but the proliferation of the PDGFRα V561D gene-introduced cells was not inhibited (FIG. 5). This result indicates that PDGFRα V561D can complement mutated EGFR-dependent proliferation of PC-9 cells. In view of the results in Examples 1 to 4, this result also indicates that any foreign oncogene can complement the proliferation of any cancer cells.

Example 6

The cells obtained by introducing the PDGFRα V561D gene into PC-9 cells in Example 4 were seeded in a 96-well plate. The cells were cultured in medium containing a PDGFRα inhibitor, imatinib at various concentrations or medium containing 1 µM gefitinib and imatinib at various concentrations for 72 hours, and then living cells were quantified by the MTS assay.

Figure 6:
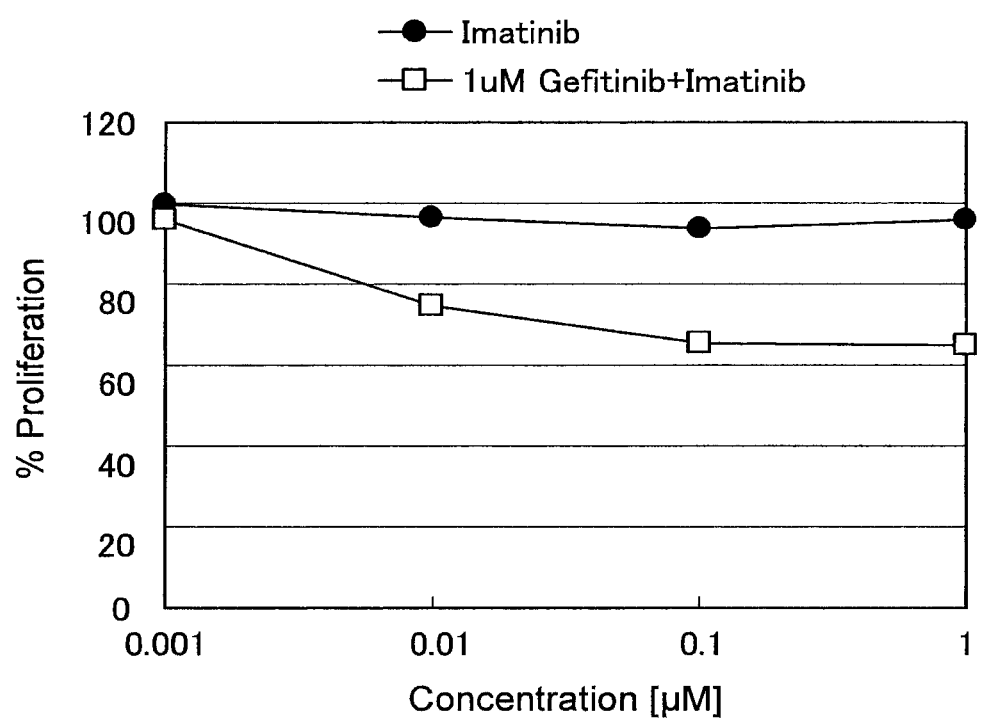
FIG. 6 is a view showing a proliferation percentage (%) of PC-9 cells transfected with the PDGFRα V561D gene in the presence of a PDGFRα inhibitor, imatinib at various concentrations (in the presence or absence of 1 µM gefitinib)

As a result, it was confirmed that the proliferation of the PDGFRα V561D gene-introduced cells was inhibited by the PDGFRα inhibitor, imatinib in a dose dependent manner in the presence of 1 µM gefitinib (FIG. 6). This result indicates that a proliferation ability of the cell line PC-9 expressing PDGFRα V561D that is a foreign oncogene depends on a functional level of the oncogene.

It was also confirmed that the proliferation of the PDGFRα V561D gene-introduced cells was inhibited in the presence of 1 µM gefitinib (FIG. 6). This result indicates that the cancer cell (PC-9 cell) retains an ability to express the inherent oncogene (mutated EGFR) and an ability to proliferate depending on the inherent oncogene.

Further this result indicates that the mutated EGFR gene (inherent oncogene) and the PDGFRα V561D gene (foreign oncogene) can act in a mutually complementary manner. Therefore, it was shown that the oncogene that works as the inherent oncogene can also work as the foreign oncogene as well as the oncogene that works as the foreign oncogene can also work as the inherent oncogene.

Example 7

Figure 7:
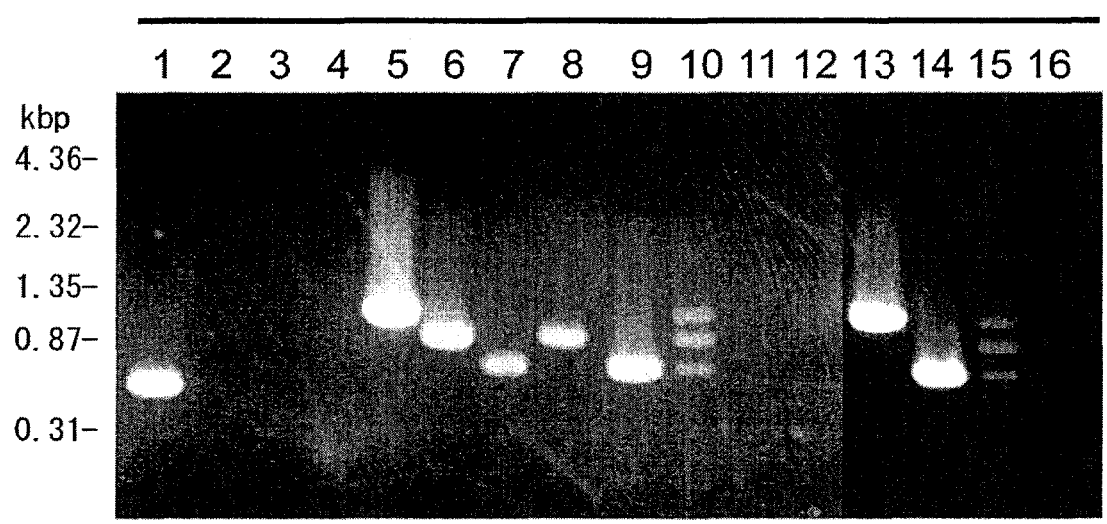
FIG. 7 is a view showing agarose gel electrophoresis of novel oncogene candidates capable of complementing mutated EGFR dependent proliferation of PC-9 cells.

In place of a plasmid which expresses the known oncogene, a gene library, SuperScript Human Stem Cell cDNA Library (supplied from Invitrogen) composed of a group of plasmids capable of expressing genes derived from a human embryonic stem cell was introduced into PC-9 cells in the same procedure as in Example 1. The cells transfected with the plasmid were cultured in the gefitinib (1 µM gefitinib)-containing medium prepared from RPMI 1640 medium supplemented with 10% fetal calf serum and an antibiotic kanamycin at 37° C. for three weeks. Total RNA was extracted from the cells selectively proliferated in the gefitinib-containing medium using an RNA purification kit (supplied from Qiagen), and a first strand cDNA was synthesized using the extracted total RNA as a template and using oligo (dT) 20 primer and a reverse transcriptase SuperScript III. The gene introduced into the proliferated PC-9 cells was amplified by PCR using an aTTB1 sequence which is a sequence commonly present in the group of the plasmids that compose the above gene library and is located in a proximity of the region upstream from the 5' end of the gene inserted into the plasmid and derived from the human embryonic stem cell as a sense primer (aTTB1 primer), an aTTB2 sequence located in the proximity of the region downstream from the 3' end of the gene derived from human embryonic stem cell as an antisense primer (aTTB2 primer), and the synthesized first strand cDNA as the template. The amplified gene was inserted into pGEM-T plasmid (supplied from Promega) by TA cloning, and *E. coli* DH5α was transformed with this gene-inserted plasmid. The transformed DH5α was seeded on an LB agar plate containing ampicillin, and incubated at 37° C. for a whole day and night. A clone that had formed a colony on the agar plate was cultured in 1 mL of an LB liquid medium containing ampicillin. The grown *E. coli* clone was collected and the plasmid was collected by plasmid Miniprep Kit (supplied from Qiagen). The collected plasmid was amplified by PCR using the aTTB1 primer and the aTTB2 primer as the template. Concerning the clone in which the amplified gene was identified by agarose gel electrophoresis (parts of results are shown in FIG. 7), a DNA sequence inserted into pGEM-T plasmid was analyzed using the collected plasmid as the template and using the sequences, T7 and Sp6 sites derived from pGEM-T as the primers. As a result, 6 genes were found as full length coding sequences (CDS) derived from the gene library which were determined as genetic sequences which could be amplified by the aTTB1 primer and the aTTB2 primer and present between them. These genes appear to be candidates of novel oncogenes capable of complementing the mutated EGFR dependent proliferation in PC-9 cells.

INDUSTRIAL APPLICABILITY

The present invention is useful for the development of the anti-cancer drugs, and the like.

The invention claimed is:

1. A method for determining whether a test gene is an oncogene, comprising:
   (a) transfecting a non-small cell lung cancer (NSCLC) cell line in a culture medium with an expression vector encoding at least one test gene, wherein the transfected NSCLC cell line expresses the test gene;
   (b) culturing the transfected NSCLC cell line under a condition which inhibits an expression or function of an EGFR oncogene or a PDGFRα oncogene that is (1) inherent to the NSCLC cell line and (2) required for proliferation of the NSCLC cell line; and
   (c) confirming whether or not the cultured NSCLC cell line proliferates,
   wherein when the cultured NSCLC cell line proliferates the test gene is determined to be a an oncogene and wherein when the cultured NSCLC cell line does not proliferate the test gene is determined not to be an oncogene.

2. The method of claim 1, wherein a single test gene is encoded by the expression vector.

3. The method of claim 1, wherein the method further comprises:
   (d) cloning a NSCLC cell line that proliferates in (c); and
   (e) identifying a test gene that is introduced into the cloned NSCLC cell line as an the oncogene.

4. The method of claim 1, wherein the method further comprises:
   (f) obtaining a test gene that is introduced into the NSCLC cell line that proliferates in (c) from the NSCLC cell line; and
   (g) cloning the obtained test gene for identifying the obtained test gene as an oncogene.

5. The method of claim 1, wherein the transfected NSCLC cell line retains an ability to express an oncogene that is inherent to the NSCLC cell line in (a) and an ability to proliferate depending on an inherent oncogene.

6. The method of claim 1, wherein the NSCLC cell line in (a) is derived from a human.

7. The method of claim 1, wherein the test gene is a transfected tyrosine kinase gene.

8. The method of claim 1, wherein the expression or function of the oncogene inherent to the NSCLC cell line is inhibited with at least one member selected from the group consisting of antisense nucleic acids for mRNA expressed from the inherent EGFR oncogene or PDGFRα oncogene, RNA interference inducible nucleic acids and aptamers, antibodies against the protein expressed from the inherent EGFR oncogene or PDGFRα oncogene, and a molecular targeting drug that targets the inherent EGFR oncogene or PDGFRα oncogene.

9. The method of claim 1, wherein the test gene is a mutant of a tumor suppressor gene.

10. The method of claim 1, wherein the NSCLC cell line is PC-9 cell.

* * * * *